United States Patent
Heyer et al.

(10) Patent No.: US 8,897,867 B2
(45) Date of Patent: Nov. 25, 2014

(54) SYSTEM AND METHOD FOR PROCESSING SIGNALS FOR THE REAL-TIME DETECTION OF A FUNCTIONAL CYCLIC ACTIVITY

(75) Inventors: Laurent Heyer, Paris (FR); Pierre-Yves Gumery, Grenoble (FR)

(73) Assignee: Assistance Publique-Hopitaux de Paris, Paris (FR)

( * ) Notice: Subject to any disclaimer, the term of this patent is extended or adjusted under 35 U.S.C. 154(b) by 420 days.

(21) Appl. No.: 13/263,180

(22) PCT Filed: Apr. 6, 2010

(86) PCT No.: PCT/FR2010/050661
§ 371 (c)(1),
(2), (4) Date: Dec. 27, 2011

(87) PCT Pub. No.: WO2010/116087
PCT Pub. Date: Oct. 14, 2010

(65) Prior Publication Data
US 2012/0095742 A1    Apr. 19, 2012

(30) Foreign Application Priority Data
Apr. 7, 2009 (FR) ........................ 09 52277

(51) Int. Cl.
A61B 5/04    (2006.01)
A61B 5/0488  (2006.01)
A61B 5/00    (2006.01)
A61B 5/08    (2006.01)

(52) U.S. Cl.
CPC ............. *A61B 5/0488* (2013.01); *A61B 5/4818* (2013.01); *A61B 5/08* (2013.01)
USPC .......................................... 600/546; 600/529

(58) Field of Classification Search
None
See application file for complete search history.

(56) References Cited

U.S. PATENT DOCUMENTS

| | | | |
|---|---|---|---|
| 4,960,118 A | 10/1990 | Pennock | |
| 6,840,907 B1 | 1/2005 | Brydon | |
| 2005/0137487 A1* | 6/2005 | Zhu et al. | 600/513 |
| 2006/0063981 A1* | 3/2006 | Sotos et al. | 600/301 |
| 2007/0118054 A1* | 5/2007 | Pinhas et al. | 600/587 |
| 2007/0270671 A1* | 11/2007 | Gal | 600/301 |
| 2008/0234773 A1* | 9/2008 | Ni et al. | 607/17 |

(Continued)

FOREIGN PATENT DOCUMENTS

| | | |
|---|---|---|
| FR | 2 921 245 A1 | 3/2009 |
| WO | 03/022149 A2 | 3/2003 |

OTHER PUBLICATIONS

International Search Report, dated Jul. 22, 2010, from corresponding PCT application.

*Primary Examiner* — Michael D'Angelo
(74) *Attorney, Agent, or Firm* — Young & Thompson (57) ABSTRACT

A system and method for processing signals for the real-time detection of a functional cyclic activity, include: elements for simultaneously receiving signals acquired by a sensor array having at least two sensors; elements for recording and pre-processing the acquired signals during a plurality of consecutive cycles; elements for identifying event combinations from the recordings of the acquired signals, enabling a calibration to be carried out, including: elements for identifying a plurality of events in the acquired signals, each signal including an identified event; elements for defining a model of the functional activity, consisting of a time order of the events and the mean delays between the events, and elements for defining a detection time window from the functional activity model.

10 Claims, 4 Drawing Sheets

(56) References Cited

U.S. PATENT DOCUMENTS

| | | | |
|---|---|---|---|
| 2008/0269625 A1* | 10/2008 | Halperin et al. | 600/508 |
| 2008/0275349 A1* | 11/2008 | Halperin et al. | 600/484 |
| 2009/0024048 A1* | 1/2009 | Lang et al. | 600/534 |
| 2009/0076557 A1* | 3/2009 | Zhang et al. | 607/4 |
| 2010/0256513 A1 | 10/2010 | Gumery et al. | |

* cited by examiner

SYSTEM AND METHOD FOR PROCESSING SIGNALS FOR THE REAL-TIME DETECTION OF A FUNCTIONAL CYCLIC ACTIVITY

BACKGROUND OF THE INVENTION

1. Field of the Invention

The present invention relates to a system and method for processing signals for the real-time detection of a periodic functional activity, in particular a respiratory muscular activity.

2. Description of the Related Art

Devices are known for monitoring the respiratory activity of a patient that comprise a single sensor measuring the respiratory muscular activity. In general, this measuring sensor is an electrode placed near the explored muscle to obtain a good signal to noise ratio. According to the article "*Neural control of mechanical ventilation in respiratory failure, Nature medicine* 1999, Sinderby et al.", the obtained quality of the signal allows real-time monitoring of a respiratory aid device, such as a ventilator, through the respiratory muscle activity (RMA) of a single muscle: the diaphragm. However, this solution is not suitable for measuring the activity of respiratory muscles other than the diaphragm. Furthermore, although it is not an intramuscular measurement (using a needle), this measurement is invasive.

Noninvasive devices are known that comprise a surface electrode, the measurement of which is not robust. To that end, noninvasive devices exist that comprise a surface electrode having a signal that is synchronized with a flow signal. According to the article "*Optimized analysis of surface electromyograms of the scalenes during quiet breathing in humans, Respiratory Physiology & Neurobiology* 2006, Hug F. et al.", these devices make it possible to obtain, precisely and robustly, the location of the triggering of inhalation activity of the scalene muscles. However, this measurement is lengthy and assumes a certain stationarity of the respiratory activity; it is consequently not adapted to real-time detection of respiratory activity and therefore cannot be used to monitor a ventilator.

BRIEF SUMMARY OF THE INVENTION

The aim of the present invention is therefore to resolve these problems by proposing a system and a method for processing signals for the real-time detection of a periodic functional activity, in particular adapted to the real-time detection of a respiratory muscular activity, noninvasively and robustly, thereby allowing exploration of the respiratory muscle function or allowing the monitoring of a respiratory aid device.

To that end, the invention relates to a system for processing signals for the real-time detection of a cyclic functional activity, the processing system comprising:
- means for simultaneously receiving, and for preprocessing and in particular filtering, signals acquired by a sensor array including at least two sensors;
- means for recording the signals acquired during a plurality of consecutive processing cycles;
- means for identifying event combinations from the recordings of the acquired signals, enabling a calibration to be carried out, including:
  - means for identifying a plurality of events in the acquired signals, each acquired signal of an acquisition means including an identified event,
  - means for defining a model of the functional activity, the model being a time order (timing chart) of the plurality of identified events and the mean delays between the identified events,
  - means for defining a detection time window from the model of the functional activity.

According to other aspects of the invention, the processing system comprises one or more of the following features:
- the plurality of consecutive processing cycles includes ten to twenty cycles,
- it also comprises means for validating the sensor array, including:
  - means for calculating match scores for each pair of acquired signals, and
  - means for comparing each calculated match score of each pair of acquired signals to a threshold value,
- it also comprises means for monitoring the functional activity for a last full cycle, including:
  - means for calculating a sliding mean of the delays between the signals acquired during a plurality of consecutive monitoring cycles, the plurality of consecutive monitoring cycles comprising the last full cycle; and
  - means for displaying the sliding mean of the delays,
- the plurality of consecutive monitoring cycles is smaller than the plurality of consecutive processing cycles,
- the monitoring means also comprise:
  - means for comparing the sliding mean of the delays to the mean of the delays calculated during the calibration step in order to detect an anomaly; and
  - means for generating and transmitting an alert signal in case of anomaly,
- it comprises signal acquisition means incorporating the sensor array,
- the signal acquisition means are cardiac muscular signal acquisition means,
- the signal acquisition means are skeletal muscular signal acquisition means,
- the signal acquisition means are respiratory muscular signal acquisition means,
- the signal acquisition means are noninvasive acquisition means,
- it also includes complementary processing means including:
  - means for receiving a signal of ventilatory activity of a patient comprising a ventilatory event;
  - means for the real-time detection of a ventilatory demand, the ventilatory demand being defined by an ordered succession of the ventilatory event and respiratory events identified using the respiratory activity model and detected in the acquired muscular signals, and
  - means for generating and transmitting a control signal to a respiratory aid device connected to a patient, and
- it also includes complementary processing means including means for acquiring information relative to the status of the respiratory aid device and means for comparing that information relative to the respiratory aid device and the detection of the patient's respiratory activity.

In this way, this system in particular makes it possible to improve the strategies and methods for monitoring and assisting the respiratory function in anesthesia and resuscitation, by using robust real-time detection of the respiratory muscular activity.

This system relates to all information taken indirectly and/or constructed using a mathematical model (therefore indirectly) that constitutes an image of a muscle contraction, such as the respiratory contraction: muscular pressure (Pmus), mechanogram, electromyogram.

This system is a means for the conjugated analysis of muscular activity information. This information is extracted indirectly, such as EMG or MMG measurements, or built by the model, such as muscular pressure (this pressure corresponding to a first filtering level of a flow signal).

This information can deliver events by level thresholding. In no case does the system measure the activity, but it detects events representative of a muscular activity, such as respiratory activity.

The invention also relates to a method for processing signals for the real-time detection of a cyclic functional activity, intended to be used by a processing system of the aforementioned type, the processing method comprising the following steps:

simultaneously receiving signals acquired by a sensor array including at least two sensors, and recording the signals acquired during a plurality of consecutive processing cycles;

calibrating, from recordings of the acquired signals, the calibration comprising the following steps:

identifying a plurality of events in the acquired signals, each acquired signal of an acquisition means including an identified event, defining a model of the functional activity, the model being a time order of the plurality of identified events and the mean delays between the identified events, defining a detection time window from the model of the functional activity.

According to other aspects of the invention, the processing method comprises one or more of the following features:

it comprises, after the calibration step, a step for monitoring the functional activity for a last full cycle, including the following steps:

calculating a sliding mean of the delays between the signals acquired during a plurality of consecutive monitoring cycles, the plurality of consecutive monitoring cycles comprising the last full cycle; and displaying the sliding mean of the delays, the acquired signals are respiratory muscular signals and the functional activity model is a respiratory activity model, and it comprises, after the calibration step, the following steps:

a step for receiving a signal of ventilatory activity of a patient comprising a ventilatory event;

a step for real-time detection of a ventilatory demand, the ventilatory demand being defined by an ordered succession of the ventilatory event and respiratory events identified using the respiratory activity model and detected in the acquired muscular signals, then a step for generating and transmitting a control signal to a respiratory aid device connected to a patient.

The inventors have novelly observed that it was possible to describe the respiratory muscular activity through an activity network of different muscles, called physiological network, and to be able to qualify that network by a limited number of sensors or signal acquisition means forming an "instrumental network."

In physiology and physiopathology, muscular respiratory activity can be described as the result of collaborations between different muscle groups. This collaboration represents highly nonlinear complex interactions that can be analyzed in terms of couplings between nonlinear oscillators. However, these couplings are modified as a function of the patient's clinical condition. The characteristics of the physiological network for activating the respiratory muscles are not known a priori and must be reevaluated for each patient and throughout the patient's clinical evolution.

BRIEF DESCRIPTION OF THE DRAWINGS

The invention will be better understood using the following description, provided solely as an example and done in reference to the appended drawings, in which.

DETAILED DESCRIPTION OF THE PREFERRED EMBODIMENTS

Figure 1:
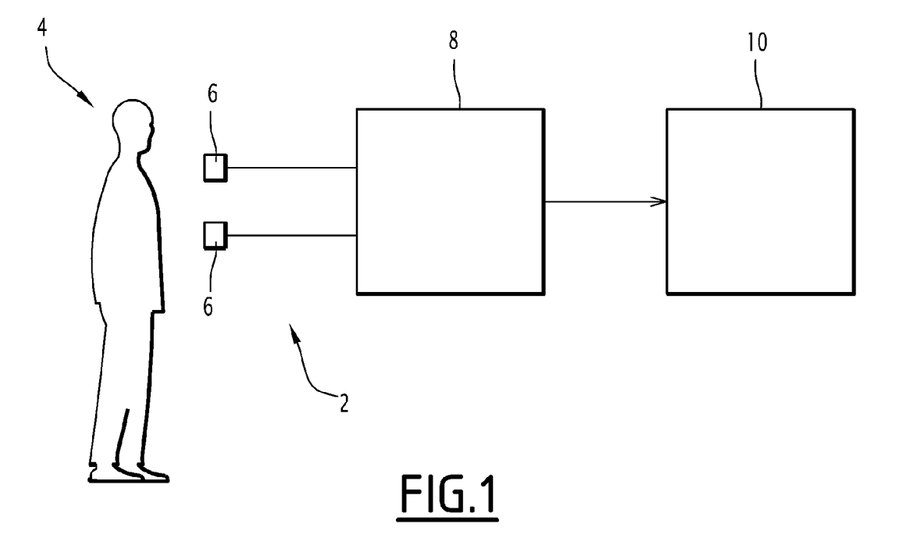
FIG. 1 shows a summary diagram illustrating the structure of a device for processing signals acquired by a sensor array for the real-time detection of a periodic functional activity according to the invention.

In FIG. 1, the system 2 for detecting the respiratory muscular activity (RMA) of a patient 4 comprises at least two acquisition means 6 or signal sensors forming an instrumental network. The signal acquisition means are means for acquiring respiratory muscular signals.

Preferably, the signal acquisition means are noninvasive means, such as surface electrodes, electromyogram (EMG) sensors, or myomechanogram (MMG) sensors.

Advantageously, each sensor, whether invasive or not, explores only one particular muscle of the muscular respiratory device.

One of these acquisition means can be a flow rate measurement from which a muscular pressure will be built using a method known by those skilled in the art.

The RMA detection system 2 also includes means 8 for processing muscular signals acquired by the acquisition means 6 using a respiratory muscular activity detection method described in detail below. The acquisition means 6 are connected to the processing means 8 of the muscular signals.

The processing means 8 of the muscular signals comprise means for simultaneously receiving signals acquired by the sensor array.

They also include means for recording the muscular signals acquired during a plurality of consecutive cycles called "processing cycles" and means for calibrating the instrumental network from the recordings of the acquired signals. This calibration consisting of identifying a combination of events, the calibration means will also be called event combination identification means.

The calibration means of the instrument network comprise means for identifying a plurality of events in the acquired signals where each acquired signal of an acquisition means includes an identified event.

The calibration means also include means for defining a respiratory muscular activation model. The model is a time order of the plurality of identified events and mean delays two by two between the identified events.

The calibration means also include means for defining a time detection window from a respiratory muscular activity model.

Furthermore, means for validating the position of the acquisition means 6 are incorporated into the signal processing means.

The means for validating the position of the acquisition means 6 include means for calculating a correlation score between two signals and means for comparing that correlation score to a value determined by an operator.

The system 2 for detecting the respiratory muscular activity also includes means 10 for monitoring the respiratory muscular activity and its real-time display. Thus, for a last full cycle, the monitoring means 10 include means for calculating a sliding mean of the delays between the signals acquired during a plurality of consecutive cycles called "monitoring cycles." This plurality of consecutive monitoring cycles incorporates the last full cycle. The monitoring means 10 also include means for displaying the sliding mean of the delays.

The monitoring means 10 can also include means for comparing the sliding mean of the delays to the mean of the delays calculated during the calibration step so as to detect an anomaly, and means for generating and transmitting an alert signal in case of anomaly.

During an exploration of the respiratory function, the traditional approach proposes to select a priori the signal of the muscle that is most representative of the studied physiological phenomenon, for example, the measurement of the primary inhalation muscle when the inhalation function is being studied. This is the case with the isolated measurement of the diaphragmatic activity, which reduces the generation of an inhalation flow upon the activity of that muscle alone.

However, having this instrumental choice overshadow the impact of the synergy between the diaphragm and the other respiratory muscles on the effectiveness of the generated inhalation becomes unsuitable in clinical situations, where the observed ventilation depends on an optimal cooperation between the different muscles.

Nevertheless, to explore a patient's muscular respiratory activity, it is no longer possible to measure the activity of all of the respiratory muscles that interact. Thus, the detection system incorporating the network formed by the acquisition means is necessarily more limited than the physiological network. It is therefore essential to make sure of the capacity of the instrumental network to effectively describe the organization of the activity of different muscles or the existence of a physiological network. The existence of such an organization then makes it possible to define the inhalation activity through a combination of different respiratory events and to ensure its robust detection.

Figure 2:
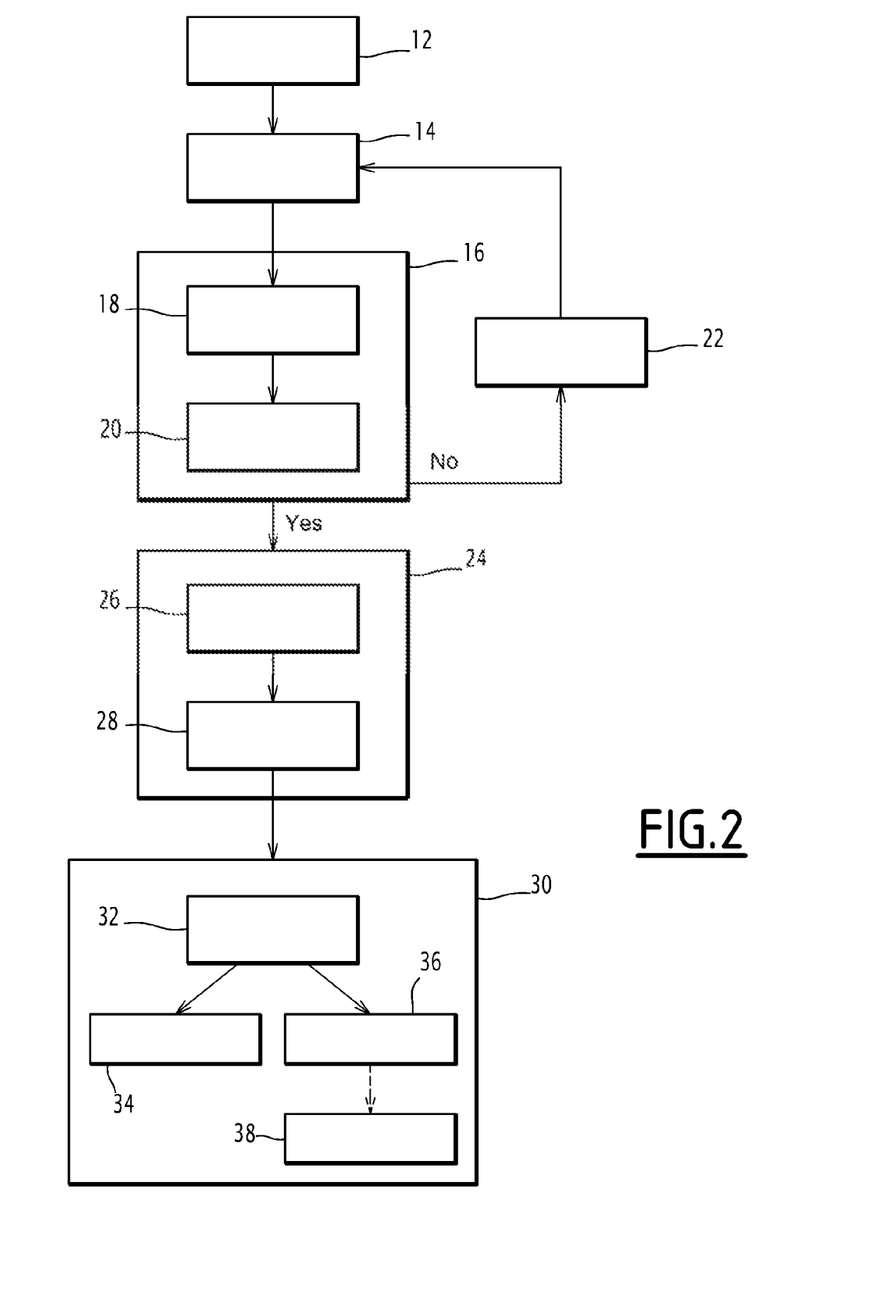
FIG. 2 is a block diagram illustrating the method for processing signals acquired by an array of sensors for the real-time detection of a periodic functional activity according to the invention.

That is the aim of the method for the real-time detection of a respiratory muscular activity of a patient as shown in FIG. 2.

In a prior step 12, the operator positions at least two acquisition means or sensors on respiratory muscles of the patient that participate in the latter's respiratory activity so that the acquisition means can detect different muscular signals.

Preferably, the sensors are positioned on different respiratory muscles. The set of sensors thus positioned forms the instrumental network.

Then, during a reception step 14, the detected muscular signals are simultaneously received by each acquisition means, online preprocessing, in particular filtering, is done, in particular to eliminate 50 Hz and EKG (electrocardiogram) disruptions, and they are recorded for a plurality of respiratory cycles in the patient's treatment.

Preferably, the plurality of respiratory treatment cycles includes 10 to 20 respiratory cycles.

The position of each acquisition means positioned on the patient is then validated 16. To that end, the potential couplings and the coherence between the channels of the instrumental network, considered two by two, i.e. between the muscular signals considered two by two, are analyzed. In fact, the analysis of the information shared by the signals coming from each sensor in the instrumental network over a long time scale (several tens of cycles) characterizes the couplings between the activities of the different explored muscles and in particular their time relationship. In a known manner, the measurement of the exchange of information is described by Pompe B. et al. in the article entitled "*Using mutual information to measure coupling in the cardiorespiratory system. IEEE Eng. Med. Biol. Mag* 1998; 17: 32-39". This information exchange measurement takes the nonlinearity of the mechanisms into account and rests on Shannon's entropy. To that end, an analysis is done on the envelopes of the signals obtained by rectification and incorporation and on sliding windows with a configurable duration. In this way, the mean envelope of each muscular signal acquired over the plurality of respiratory cycles is developed in a known manner, and a match score or coupling level is calculated 18 between each pair of muscular signals.

Lastly, each calculated match score is compared 20 to a threshold value, determined beforehand by the operator.

If the match score is greater than the threshold value, the two muscular signals are well-correlated, which validates the position of the two acquisition means on the patient's respiratory muscles.

If not, the muscular signals do not match, and then the operator modifies 22 the position of at least one acquisition means. The operator can modify the position of at least one acquisition means on the muscle where it was already positioned, or can move it onto another respiratory muscle or eliminate it. After having modified the position of at least one acquisition means, the preceding steps are carried out again until relevant muscular signals are obtained, i.e. all correlated with each other and participating in the respiratory muscular activity of the patient. The obtainment of relevant muscular signals validates the position of all of the acquisition means used on the patient.

According to one alternative, the validation 16 of the sensor positions is done manually by the operator.

After step 16 for validating the position of all of the acquisition means, in step 24 the device for detecting the patient's respiratory muscular activity is calibrated or qualified.

To that end, from the recordings of the acquired muscular signals, a respiratory muscular activation model of the patient as equipped with the acquisition means 6 is defined 26.

In fact, the calculation of the correlation functions of the muscular signals defines a time order for activation of the different respiratory muscles.

To that end, on each muscular signal, the beginning of an event representative of that activation is identified.

Then, from the envelopes of the muscular signals, the mean delay between two events identified in two signals is determined 26 for all of the muscular signals.

Preferably, the measurement of the mean delays more specifically related to the beginning of activities of the different signals representative of the organization of a respiratory event, such as the inhalation request, is obtained by the coherent accumulation method, *Respiratory Physiology & Neurobiology* 2006, Hug F. et al. To implement this method, an additional flow measurement is also used.

For example, a standard criterion is used to determine the beginning of the activation of a muscle, i.e.: the moment of an activation event in a signal is determined by the calculation of the local drift or slope of the envelope of the signal and its value is compared to a reference value chosen by the operator.

Figure 3:
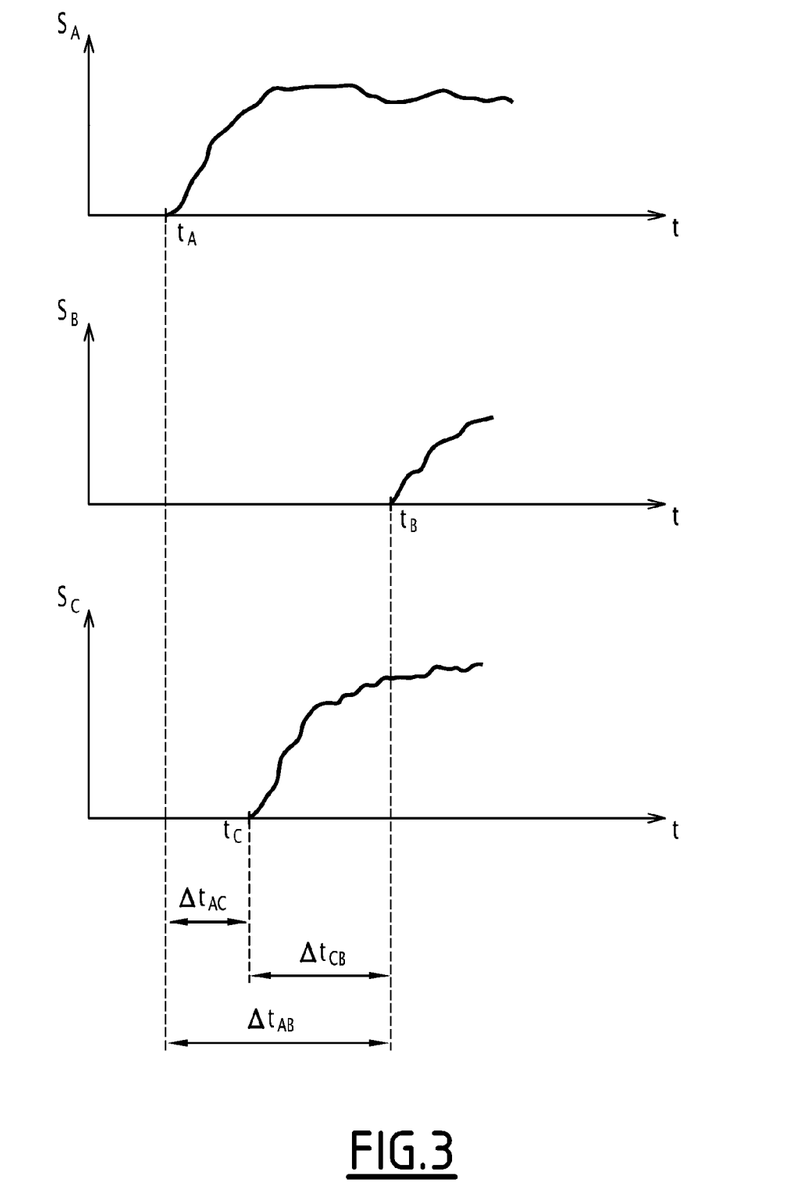
FIG. 3 is a diagrammatic illustration of the signals acquired by a sensor array and the model obtained during performance of the signal processing method as illustrated in FIG. 2.

As an example, FIG. 3 illustrates the intensity as a function of time of three signals $S_A$, $S_B$ and $S_C$ acquired on different muscles A, B, C. The order indicates the activation of muscle A before that of muscle C, and lastly that of muscle B at respective moments $t_A$, $t_B$ and $t_C$. The mean delays are denoted $\Delta t_{AB}$, $\Delta t_{AC}$ and $\Delta t_{CB}$.

This method can also be implemented by using the end of activation intensity of the muscles or a muscular pressure variation as event.

The set of mean times/delays and the time order to activate the respiratory muscles defines a respiratory muscular activity (RMA) model of the patient, also called activation identification model and generally shown by a time chart.

These relationships determine the time scale for the analysis of the respiratory activity, for example the patient's inhalation activity.

A time detection window is defined 28 from these mean delays/times, for example the beginning of the time detection window coincides with the first identified event and its length is the largest mean delay, i.e. between the first and last identified activation events of the respiratory muscles.

The step 24 for calibrating the device for detecting the patient's respiratory muscular activity is then finished.

This step 24 makes it possible to qualify the capacity of the acquisition means 6 distributed on various muscles involved in the patient's respiratory activity to show an activation model of the respiratory muscles of the patient 4. It enables the selection of the most relevant paths for qualification of the array and lastly identifies the analysis time scale needed to characterize respiratory events, and in particular inhalation events.

Once the system is qualified and calibrated, it can be used for real-time monitoring of the patient's respiratory muscular activity.

To that end, the time detection window is updated to monitor 30 the patient's respiratory muscular activity upon each new respiratory cycle.

Thus, the mean delays over the last M consecutive respiratory cycles between the acquired muscular signals are calculated 32 while producing a sliding mean over the last M values of the delays between each pair of muscular signals. The number M is determined by the operator. The number of monitoring cycles is smaller than the number of treatment cycles. Advantageously, it is between 8 and 12 respiratory cycles and preferably, M is equal to ten.

Then, the values are displayed 34 on the monitoring means 10 of the muscular activity detection device.

Subsequently, the values of these delays can be compared 36 to the values calculated during the calibration step or to reference values determined by the operator in order to detect an anomaly, and in case of anomaly an audio and/or visual signal can be emitted 38.

This monitoring of the patient's respiratory muscular activity is useful for the anesthesiologist and provides information on the patient's condition. In this respect, the clinical information that can be extracted is for example a disorganization of the respiratory function, respiratory discomfort or an anesthetic state.

The device for detecting respiratory muscular activity is then a device for the real-time exploration of the patient's respiratory operation.

Figure 4:
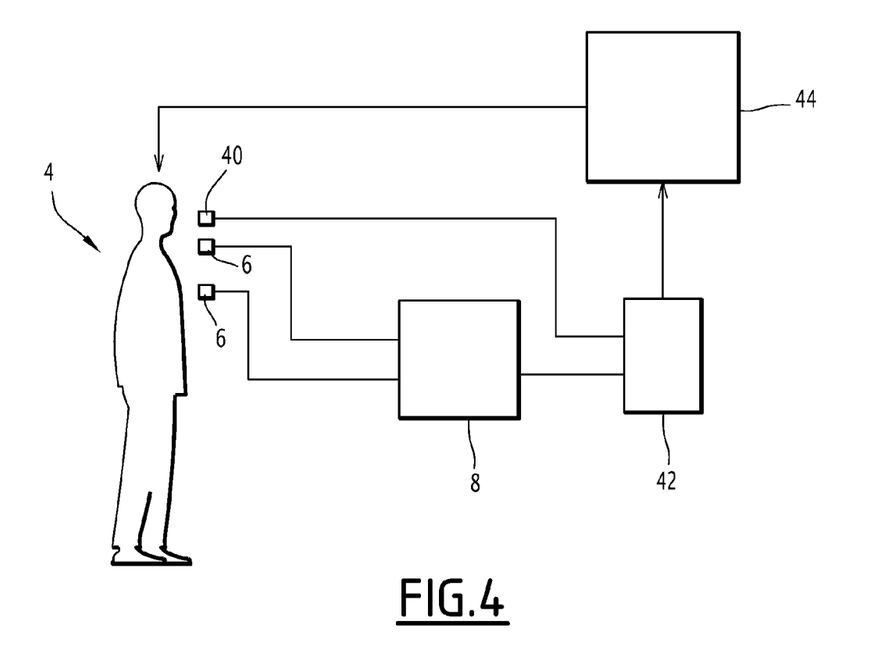
FIG. 4 shows a summary diagram illustrating a respiratory aid device steered by a device for processing signals acquired by a sensor array for the real-time detection of a periodic functional activity.

According to another embodiment shown in FIG. 4, the device for detecting respiratory muscular activity also comprises complementary processing means 42 including acquisition means 40 a signal representing a ventilatory activity by the patient and means for receiving that ventilatory signal. This signal includes a ventilatory event. Preferably, these ventilatory acquisition means comprise at least one air flow sensor installed at the patient's mouth.

The complementary processing means 42 also comprise means for the real-time detection of a ventilatory demand. The ventilatory demand is defined by an ordered succession of the ventilatory event and respiratory events identified using the respiratory activity model and detected in the acquired muscular signals.

The complementary processing means 40 also comprise means for generating and transmitting a control signal to a respiratory aid device 44 connected to a patient.

Figure 5:
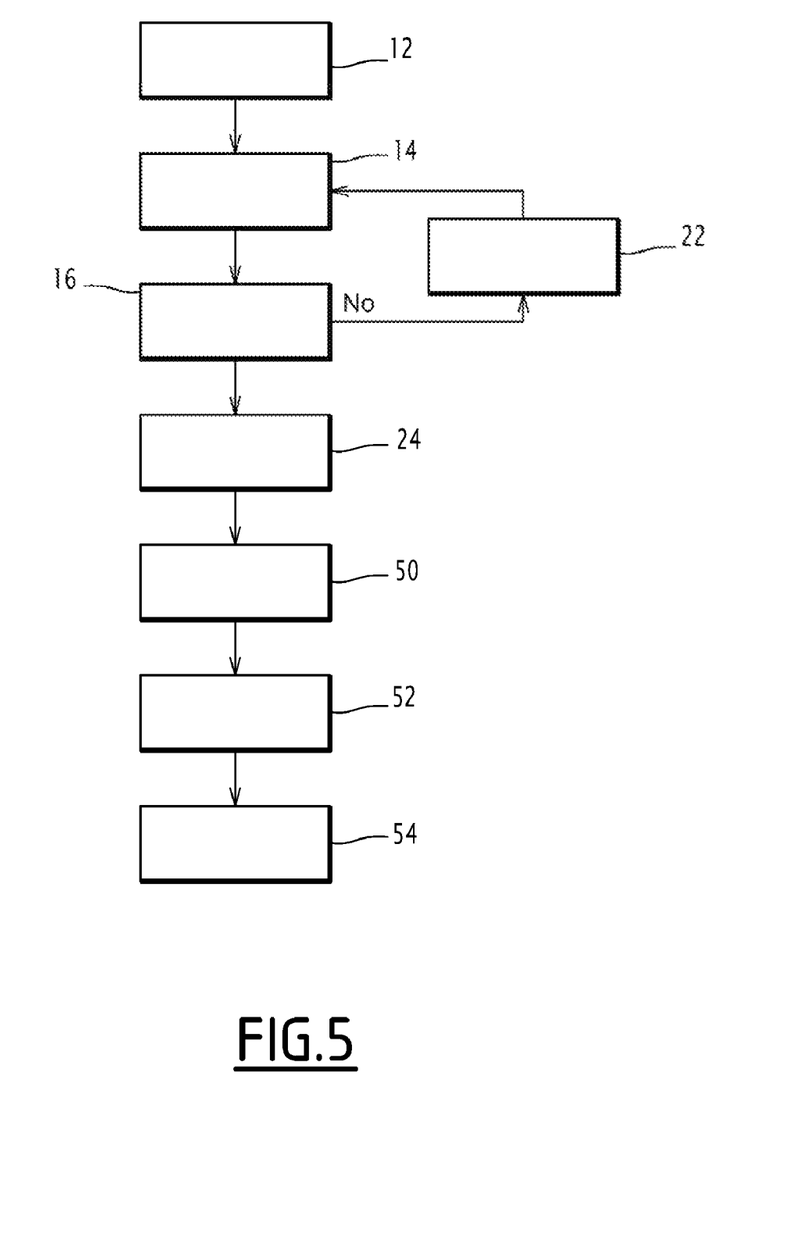
FIG. 5 is a block diagram illustrating the signal processing method according to the invention and carried out by the device illustrated in FIG. 4.

This device implements the method illustrated in FIG. 5 and detailed below. The prior steps for calibrating 24 the device are identical to those previously described.

The calibration 24 or qualification of the instrumental network provides a window adapted to the patient's behavior for the robust detection of a respiratory demand, preferably an inhalation demand, such as the combination of unitary respiratory events in a given detection window. This combination can correspond to a time sequence of unitary activations and/or a logical combination of those different activations.

Calibrating 24 the device makes it possible to define 26 the respiratory muscular activation model of the patient as equipped with the acquisition means.

This model can be used for the robust real-time detection of a respiratory event, preferably an inhalation demand by the patient, and thus for triggering an insufflation of air to the patient through a ventilatory aid device.

To that end, any detection of the inhalation demand must be done in a time shorter than an electromechanical period that will for example be defined as the difference between the objective perception of the inhalation activity through the sensor array and the passage past zero of the patient's air flow.

This is why a ventilatory activity is measured 50 using ventilatory acquisition means 40 installed on the patient 4, for example close to the patient's mouth.

This ventilatory activity measurement 50 and the respiratory muscular activity detection 52 are used to generate 54 a control signal for the respiratory aid device 44. In fact, when an inhalation demand is detected in a time shorter than the electromechanical period, a control signal is emitted toward the respiratory aid device 44 to trigger the insufflation of air to the patient.

According to one alternative, the measurement of the respiratory muscular activity and the detection of the respiratory event are used to detect an anomaly in the operation of the respiratory aid device, for example a desynchronization between the previously-programmed device and the patient. In fact, the precision of the detection of an inhalation activity being lower than the electromechanical period, it can be exploited to evaluate the quality of the adjustment between the inhalation activity of a patient and the patient's respiratory aid device. In that operating mode, when an adjustment quality flaw between the patient's respiratory activity, on the one hand, and the patient's respiratory aid device, on the other, is detected, an audio or visual alert signal is emitted to notify the operator. To that end, the system 2 comprises means for acquiring information relative to the status of the respiratory aid device and means for comparing that information relative to the respiratory aid device and the detection of the patient's respiratory activity, such as an inhalation demand.

One skilled in the art will understand that irrespective of the usage mode, the method provides for the detection of events in the time detection window from the functional activity model, the latter being a sliding window, and will understand that the device includes means for detecting events in the detection window.

Thus, a system and a method according to the invention make it possible to ensure a robust measurement of a patient's respiratory muscular activity from noninvasive real-time measurements on several muscles making it possible in particular to steer the triggering of a respiratory aid device.

In fact, owing to this method and this device, the detection of a combination of respiratory events from a noninvasive sensor array sufficient to qualify the activation model of the studied patient's respiratory muscles is substituted for the detection of a respiratory event from the signal of a single sensor. This approach through the joint analysis of events allows more effective discrimination between the respiratory activity and the parasitic muscular activities (i.e. those not participating in respiration).

This solution has several advantages relative to the prior methods. On the one hand, it provides robust detection of the inhalation demand from noninvasive sensors while preserving the time precision acquired for the detection on a single signal. And on the other hand, it represents an adaptive detection solution that accounts for the diversity and evolution of the patient's respiratory muscular activation mode and the instrumental capacity of the sensor array developed for the functional exploration.

Such a detection device for a respiratory muscular activity can be used, for example, to assist in deciding whether to cut respiratory aid for patients with vigilance difficulties. In fact, in such patients, the lengthening of the activation delay is associated with a deterioration of the effectiveness of the respiratory muscular activity and the need to maintain mechanical respiratory aid. By making it possible to detect such lengthening of the activation delay, in particular the activation delay between various inhalation muscles distributed according to a rostrocaudal gradient, the inventive device and method therefore make it possible to help make the right decision.

The invention has been described in the context of the detection of an inhalation demand by the patient. However, it obviously applies to the detection of any other respiratory event, for example an exhalation demand by the patient.

The invention is also applicable to other fields, for example motor rehabilitation, aging and/or cardiology pathologies, and more generally all fields where a "functional activity model" and its alteration in a pathology can be identified. To that end, the signal acquisition means are in particular means for acquiring cardiac muscular or skeletal muscular signals.

The invention claimed is:

1. A system for processing signals for the real-time detection of a cyclic functional activity, the processing system comprising:
    a signal acquisition means forming an instrumental network including at least two sensors;
    one or more processing devices configured to:
    simultaneously receive signals acquired by the signal acquisition means,
        record and preprocess the acquired signals during a plurality of consecutive processing cycles,
        identify event combinations from recordings from the acquired signals, enabling a calibration to be carried out by the one or more processing devices, the calibration being carried out by:
            identifying a plurality of events in the acquired signals, each one of the events corresponding to an activation of a muscle and each acquired signal of the signal acquisition means including a plurality of identified events,
            defining a model of the cyclic functional activity, the model being a timing chart consisting of a time order of the plurality of identified events and mean delays between the identified events,
            defining a detection time window from the model of the cyclic functional activity, and
            detecting events into the detection time window taking into account the model of the cyclic functional activity; and
    a monitoring device configured to monitor the cyclic functional activity for a last full cycle, the monitoring device configured to:
        calculate a sliding mean of the delays between the events detected into the signals acquired during a plurality of consecutive monitoring cycles, the plurality of consecutive monitoring cycles comprising the last full cycle,
        display the sliding mean of the delays,
        compare the sliding mean of the delays to the mean of the delays calculated during the calibration in order to detect an anomaly, and
        generate and transmit an alert signal when the anomaly is detected.

2. The processing system according to claim 1, wherein the plurality of consecutive processing cycles includes ten to twenty cycles.

3. The processing system according to claim 1, wherein the one or more processing devices is configured to validate the sensor array, by
    calculating match scores for one or more pairs of the acquired signals, and
    comparing each of the calculated match scores of each of the pairs of the acquired signals to a threshold value.

4. The processing system according to claim 1, wherein the plurality of consecutive monitoring cycles is smaller than the plurality of consecutive processing cycles.

5. The processing system according to claim 1, wherein the signal acquisition means are cardiac muscular signal acquisition means.

6. The processing system according to claim 1, wherein the signal acquisition means are cardiac skeletal muscular signal acquisition means.

7. The processing system according to claim 1, wherein the signal acquisition means are respiratory muscular signal acquisition means.

8. The processing system according to claim 1, wherein the signal acquisition means are noninvasive acquisition means.

9. The processing system according to claim 7, further comprising a complementary processing device configured to:
    receive a signal of ventilatory activity of a patient comprising a ventilatory event;
    detect, in real-time, a ventilatory demand, the ventilatory demand being defined by an ordered succession of the ventilatory event and respiratory events identified using the respiratory activity model and detected in the acquired muscular signals, and
    generate and transmit a control signal to a respiratory aid device connected to the patient.

10. The processing system according to claim 7, wherein the complementary processing device is configured to acquire information relative to the status of the respiratory aid device and compare that information relative to the respiratory aid device and the detection of the patient's respiratory activity.

* * * * *